US007928193B2

(12) United States Patent
Cortese et al.

(10) Patent No.: US 7,928,193 B2
(45) Date of Patent: Apr. 19, 2011

(54) ANTIGEN BINDING PROTEINS DIRECTED AGAINST SCAVENGER RECEPTOR B1 THAT INHIBIT HCV REPLICATION

(75) Inventors: Riccardo Cortese, Rome (IT);
Alessandra Luzzago, Rome (IT);
Alfredo Nicosia, Rome (IT);
Alessandra Vitelli, Rome (IT)

(73) Assignee: Istituto di Ricerche di Biologia Molecolare P. Angeletti S.p.A., Rome (IT)

( * ) Notice: Subject to any disclaimer, the term of this patent is extended or adjusted under 35 U.S.C. 154(b) by 351 days.

(21) Appl. No.: 11/631,765

(22) PCT Filed: Jul. 1, 2005

(86) PCT No.: PCT/EP2005/007160
§ 371 (c)(1),
(2), (4) Date: Jan. 3, 2007

(87) PCT Pub. No.: WO2006/005465
PCT Pub. Date: Jan. 19, 2006

(65) Prior Publication Data
US 2008/0286275 A1 Nov. 20, 2008

Related U.S. Application Data

(60) Provisional application No. 60/586,356, filed on Jul. 8, 2004.

(51) Int. Cl.
*C07K 14/00* (2006.01)
(52) U.S. Cl. ............... 530/350; 530/387.1; 536/23.4; 435/69.7
(58) Field of Classification Search .................. None
See application file for complete search history.

(56) References Cited

U.S. PATENT DOCUMENTS

| 2003/0073149 A1* | 4/2003 | Archer et al. ............. 435/7.92 |
| 2005/0019751 A1* | 1/2005 | Cortese et al. .................. 435/5 |

FOREIGN PATENT DOCUMENTS
WO      WO 03/040726       5/2003

OTHER PUBLICATIONS

Flint et al., "Characterization of Hepatitis C Virus E2 Glycoprotein Interaction with a Putative Cellular Receptor, CD81," Journal of Virology, vol. 73 No. 8, pp. 6235-6244 (Aug. 1999).*
Meuleman et al., "Anti-CD81 antibodies can prevent a hepatitis C virus infection in vivo," Hepatology, vol. 48 No. 6, pp. 1761-1768 (Dec. 2008).*
Rduikoff et al., "Single amino acid substitution altering antigen-binding specificity," Proceedings of the National Academy of Sciences, USA, vol. 79 No. 6, pp. 1979-1983 (Mar. 1982).*
Webster et al., "Development of novel treatments for hepatitis C," The Lancet, col. 9 No. 2, pp. 108-117 (Feb. 2009).*
Acton, S. et al. "Identification of Scavenger Receptor SR-BI as a High Density Lipoprotein Receptor", Science, 1996, vol. 271, pp. 518-520.
Agnello, V. et al. "Hepatitis C virus and other Flaviviridae viruses enter cells via low density lipoprotein receptor", PNAS, 1999, vol. 96, pp. 12766-12771.
Azzazy, H. et al. "Phage display technology: clinical applications and recent innovations", Clinical Biochemistry, 2002, vol. 35, pp. 425-445.
Bartosch, B. et al. "Cell Entry of Hepatitis C Virus Requires a Set of Co-receptors That Include the CD81 Tetraspanin and the SR-B1 Scavenger Receptor", The Journal of Biological Chemistry, 2003, vol. 278, pp. 41624-41630.
Berger, M. et al. "Therapeutic Applications of Monoclonal Antibodies", The American Journal of the Medical Sciences, 2002, vol. 324, pp. 14-30.
Boel, E. "Functional human monoclonal antibodies of all isotypes constructed from phage display library-derived single-chain Fv antibody fragments", Journal of Immunological Methods, 2000, vol. 239, pp. 153-166.
De Francesco, R. et al. "Approaching a new era for hepatitis C virus therapy: inhibitors of the NS3-4A serine protease and the NS5B RNA-dependent RNA polymerase", Antiviral Research, 2003, vol. 58, pp. 1-16.
Krieger, M. "Scavenger receptor class B type I is a multiligand HDL receptor that influences diverse physiologic systems", The Journal of Clinical Investigation, 2001, vol. 108, pp. 793-797.
Liang, M. et al. "Baculovirus expression cassette vectors for rapid production of complete human IgG from phage display selected antibody fragments", Journal of Immunological Methods, 2001, vol. 247, pp. 119-130.
Patel, A. et al. "Construction and characterization of chimeric hepatitis C virus E2 glycoproteins: analysis of regions critical for glycoprotein aggregation and CD81 binding", Journal of General Virology, 2000, vol. 81, pp. 2873-2883.
Persic, L. et al. "An integrated vector system from the eukaryotic expression of antibodies or their fragments after selection from phage display libraries", Gene, 1997, vol. 187, pp. 9-18.
Piero, P. et al. "Binding of Hepatitis C Virus to CD81", Science, 1998 vol. 282, pp. 938-941.
Scarselli, E. et al. "The human scavenger receptor class B type I is a novel candidate receptor for the hepatitis C virus", The EMBO Journal, 2002, vol. 21, pp. 5017-5025.
Temel, R. et al. "Scavenger receptor calss B, type 1 (SR-BI) is the major route for the delivery of high density lipoprotein cholesterol to the steriodogenic pathway in cultured mouse adrenocortical cells", Proc. Natl. Acad. Sci., 1997, vol. 94, p. 13600-13605.
Urban, S. et al. "Scavenger Receptor BI Transfers Major Lipoprotein-associated Phospholipids into the Cells", The Journal of Biological Chemistry, 2000, vol. 275, pp. 33409-33415.
Walker, M. et al. "Hepatitis C virus therapies: current treatments, targets and future perspectives", Antiviral Chemistry & Chemotherapy, 2003, vol. 14, pp. 1-21.

(Continued)

*Primary Examiner* — Zachariah Lucas
*Assistant Examiner* — Michelle Horning
(74) *Attorney, Agent, or Firm* — Melissa B. Wenk; Sheldon O. Heber

(57) ABSTRACT

The present invention features antigen binding protein that bind to a SR-BI target region identified herein as a region involved in HCV E2 binding. Identified target regions are regions bound by a single-chain antibody of SEQ ID NOs: 1, 2, 3 or 4.

6 Claims, 7 Drawing Sheets

OTHER PUBLICATIONS

Yoo, E. et al. "Myeloma expression systems", Journal of Immunological Methods, 2002, vol. 261, pp. 1-20.

Patent Abstracts of Japan, "Monoclonal Antibody and Method for Producing the Same", vol. 2003, No. 12, (JP 2004 331633, Nov. 25, 2004).

Chowdhury et al., Engineering scFvs for Improved Stability, p. 237-254 in Recombinant Antibodies for Cancer Therapy Methods and Protocols, (Eds. Weschof and Krauss) Humana PRess, Totowa, New Jersey 2003.

E.g., O'Brien, et al., Humanization of Monoclonal Antibodies by CDR Grafting, p. 81-100, From *Methods* in Molecular Biology vol. 207: Recombinant antibodies for Cancer Therapy: Methods and Protocols (Eds Welschof and Krauss) Humana Press, Totowa, New Jersey 2003.

* cited by examiner

Heavy chain sequence alignment

```
               FW1                                CDR1           FW2                    CDR2
SEQ 1 (con)  EVQLVQSGAEVRKPGATVKISCKLTGDTFTDYFIF--WLQLAPGKGLQWMGLIDPKDAQTIYAEKFQG
SEQ 4 (con)  EVQLVQSGAEVRKPGTAVKISCKVAGDTFTDYFIY--WLQQAPGKGPEWMGLIDPKDAQTIYAEKFQG
SEQ 3 (con)  EVQLVETGAEVKKPGSSVKVSCKASGDTLSSHAII--WVRQAPGQGLEWMGGIIPIFRTVNYAQKFQG
SEQ 2 (con)  QVQLQESGPGLVKPSETLSLNCTVSGGSISSSSYYWGWIRQPPGKGLEWIGSVYYTGNTYYNPSLKS FW3                                       CDR3              FW4
SEQ 1 (con)  RVAITADTSTDTAYMEVSSLRSEDTAVYYCATDSVGAAGF-----DVWGRGTMVTVSS
SEQ 4 (con)  RVAITADTSTDTAYMELSSLKSEDTAVYYCATDSVGSAGF-----DVWGQGTLVTVSS
SEQ 3 (con)  RVTITADDSTSTAYMELNDLRSEDTAVYYCAKTLNEGLPW-----DYWGQGTLVTVSS
SEQ 2 (con)  RVTMSVDTSKNQFSLKLNSVTAADTAVYYCARHVLGGWEVSQRFDYWGRGTLVTVSS linker
SEQ 1 (con)  GGGGSGGGGSGGGGSA
SEQ 4 (con)  GGGGSGGGGSGGGGSA
SEQ 3 (con)  GGGGSGGGGSGGGGSA
SEQ 2 (con)  GGGGSGGGGSGGGGSA
```

FIG. 3A

Light chain sequence alignment

```
              FW1                              CDR1                    FW2              CDR2
SEQ 1 (con)   LPVLTQPPSASGAPGQRVTFSCSGSGSNIGSYTVNWYQQLPGAAPRLLMHTTDQRAS
SEQ 4 (con)   LPVLTQPPSASGAPGQRVTFSCSGSGSNIGSYTVNWYQQLPGAAPRLLMHTTDQRAS
SEQ 3 (con)   QSVLTQPPGASGAPGQRVTISCSGDSSNIESYAVNWYQQVPGMAPKLLIYRDNQRPS
SEQ 2 (con)   QSVLTQPPSASGTPGQRVTISCSGSSSNIGSNPVNWYQQLPGTAPKLLIHTNNQRPS FW3                           CDR3                       FW4
SEQ 1 (con)   GAPDRFSGSKSGTSASLAITGLQSEDEADYFCAAWDDSLDGPVFGGGTKLTVL
SEQ 4 (con)   GVPDRFSGSKSGTSASLAITGLQSEDEADYFCAAWDDSLDGPVFGGGTKLTVL
SEQ 3 (con)   GVPDRFSGSRSGTSASLAISGLQSEDEADYYCGSWDDNLNGPTFGGGTKVTVL
SEQ 2 (con)   GVPDRFSGSKSGTSASLAISGLLSEDEADYYCAAWDDSLNAYVFGTGTKVTVL
```

FIG. 3B

```
GAAGTGCAGCTGGTGCAGTCTGGGGCTGAAGTGAGGAAGCCTGGGGCTACAGTGAAGATCTCCTGCAAATTGACT
GGAGACACATTCACCGACTACTTCATATTTTGGCTACAACTGGCCCCTGGAAAAGGGCTTCAGTGGATGGGACTT
ATTGATCCTAAAGATGCTCAAACAATATATGCAGAGAAGTTCCAGGGCAGAGTCGCCATCACCGCGGACACGTCT
ACCGACACAGCCTACATGGAAGTGAGCAGCCTGAGATCTGAAGACACGGCCGTCTATTACTGTGCAACAGATTCT
GTGGGAGCTGCTGGATTTGATGTCTGGGGCCGAGGGACAATGGTCACCGTCTCGAGTGGAGGCGGCGGTTCAGGC
GGAGGTGGCTCTGGCGGTGGCGGAAGTGCACTGCCTGTGCTGACTCAGCCCCCTCAGCGTCTGGGGCCCCGGG
CAGAGGGTCACCTTCTCTTGTTCTGGAAGCGGCTCCAACATCGGAAGTTATACTGTAAACTGGTACCAGCAGCTC
CCAGGAGCGGCCCCCAGACTCCTCATGCATACTACTGATCAGCGGGCCTCAGGGGCGCCTGACCGATTCTCTGGC
TCCAAGTCTGGCACCTCAGCCTCCCTGGCCATCACTGGGCTCCAGTCTGAGGATGAGGCTGACTATTTCTGTGCA
GCATGGGATGACAGCCTGGATGGTCCGGTGTTCGGCGGAGGGACCAAGCTGACCGTCCTA
```

FIG. 4A

```
CAGGTGCAGCTGCAGGAGTCGGGCCCAGGACTGGTGAAGCCTTCGGAGACCCTGTCCCTCAACTGCACTGTCTCT
GGTGGCTCCATCAGCAGTAGTAGTTACTACTGGGGCTGGATCCGCCAGCCCCCAGGGAAGGGGCTGGAGTGGATT
GGGAGTGTCTATTATACTGGGAACACCTACTACAACCCGTCCCTCAAGAGTCGAGTCACCATGTCCGTCGACACG
TCCAAGAACCAGTTCTCCCTGAAGCTGAACTCCGTGACCGCCGCAGACACGGCTGTGTACTATTGTGCGAGACAT
GTTTTAGGGGGAGGGTGGGAAGTAAGTCAGAGATTTGACTACTGGGGCCGGGGCACCCTGGTCACCGTCTCGAGT
GGAGGCGGCGGTTCAGGCGGAGGTGGCTCTGGCGGTGGCGGAAGTGCACAGTCTGTGTTGACGCAGCCGCCCTCA
GCGTCTGGGACCCCCGGGCAGAGGGTCACCATCTCTTGTTCTGGAAGCAGCTCCAACATCGGAAGTAATCCTGTA
AACTGGTACCAGCAGCTCCCAGGAACGGCCCCCAAACTCCTCATCCATACTAACAATCAGCGGCCCTCAGGGGTC
CCTGACCGATTCTCTGGCTCCAAGTCTGGCACCTCAGCCTCCCTGGCCATCAGTGGGCTCCTGTCTGAGGATGAG
GCTGATTATTACTGTCAGCATGGGATGACAGCCTGAATGCTTATGTCTTCGGAACTGGGACCAAGGTCACCGTC
CTA
```

FIG. 4B

```
GAGGTGCAGCTGGTGGAGACTGGGGCTGAGGTGAAGAAGCCTGGGTCCTCGGTGAAGGTCTCCTGCAAGGCTTCC
GGAGACACCCTCAGCAGTCATGCTATCATCTGGGTGCGACAGGCCCCTGGACAAGGGCTTGAGTGGATGGGAGGG
ATCATCCCTATCTTTCGTACAGTAAATTACGCACAGAAATTCCAGGGCAGAGTCACGATTACCGCGGACGATTCC
ACGAGCACGGCCTACATGGAACTCAATGACTTGAGATCTGAGGACACGGCCGTCTATTACTGTGCGAAAACGCTA
AATGAGGGGTTACCGTGGGACTACTGGGGCCAGGGCACCCTGGTCACCGTCTCGAGTGGAGGCGGCGGTTCAGGC
GGAGGTGGCTCTGGCGGTGGCGGAAGTGCACAGTCTGTGCTGACTCAGCCACCCGGAGCGTCTGGGGCCCCCGGG
CAGAGGGTCACCATCTCTTGTTCTGGAGACAGTTCCAACATCGAGAGTTATGCTGTAAATTGGTACCAGCAAGTC
CCTGGAATGGCCCCCAAACTCCTCATCTATCGTGATAATCAGCGCCCCTCAGGGGTCCCTGACCGATTCTCTGGC
TCCAGGTCTGGCACCTCAGCCTCCCTGGCCATCAGTGGGCTCCAGTCTGAGGATGAGGCTGATTATTACTGTGGA
TCATGGGATGACAATTTGAATGGCCCCACGTTCGGCGGAGGGACCAAGGTCACCGTCCTA
```

FIG. 4C

```
GAGGTGCAGCTGGTGCAGTCTGGGGCTGAGGTGAGGAAGCCTGGGACTGCAGTGAAAATCTCCTGCAAGGTTGCT
GGCGACACATTCACCGACTACTTCATATACTGGCTGCAACAGGCCCCTGGAAAAGGGCCTGAGTGGATGGGACTT
ATTGATCCTAAGGATGCTCAGACAATATACGCAGAGAAGTTCCAGGGCAGAGTCGCCATAACCGCGGACACGTCT
ACGGACACAGCTTACATGGAACTGAGCAGCCTGAAGTCTGAGGACACGGCCGTGTATTACTGTGCAACAGATTCT
GTGGGATCTGCTGGTTTTGATGTCTGGGGCCAGGGCACCCTGGTCACCGTCTCGAGTGGAGGCGGCGGTTCAGGC
GGAGGTGGCTCTGGCGGTGGCGGAAGTGCACTGCCTGTGCTGACTCAGCCCCCCTCAGCGTCTGGGGCCCCGGG
CAGAGGGTCACCTTCTCTTGTTCTGGAAGCGGCTCCAACATCGGAAGTTATACTGTAAACTGGTACCAGCAGCTC
CCAGGAGCGGCCCCCAGACTCCTCATGCATACTACTGATCAGCGGGCCTCAGGGGTGCCTGACCGATTCTCTGGC
TCCAAGTCTGGCACCTCAGCCTCCCTGGCCATCACTGGGCTCCAGTCTGAGGATGAGGCTGACTATTTCTGTGCA
GCATGGGATGACAGCCTGGATGGTCCGGTGTTCGGCGGAGGGACCAAGCTGACCGTCCTA
```

FIG. 4D

```
MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQEKCYLFWSSSKKGSKDKEAIQAYSESLMTSAPKGSVLQEAKL
```

FIG. 5

ANTIGEN BINDING PROTEINS DIRECTED AGAINST SCAVENGER RECEPTOR B1 THAT INHIBIT HCV REPLICATION

CROSS-REFERENCE TO RELATED APPLICATIONS

The present application claims the benefit of U.S. Provisional Application No. 60/586,356, filed Jul. 8, 2004 hereby incorporated by reference herein.

BACKGROUND OF THE INVENTION

The references cited in the present application are not admitted to be prior art to the claimed invention.

It is estimated that about 3% of the world's population is infected with the hepatitis C virus (HCV). (Wasley et al., *Semin. Liver Dis.* 20:1-16, 2000.) HCV exposure results in an overt acute disease in a small percentage of cases, while in most instances the virus establishes a chronic infection causing liver inflammation and slowly progresses into liver failure and cirrhosis. (Strader et al., *ILAR J.* 42:107-116, 2001.) Epidemiological surveys indicate an important role for HCV in the onset of hepatocellular carcinoma. (Strader et al., *ILAR J.* 42:107-116, 2001.)

HCV can be classified into a number of distinct genotypes (1 to 6), and subtypes (a to c). The distribution of the genotypes and subtypes varies both geographically and between risk groups. (Robertson et al., *Arch Virol.* 143:2493-2503, 1998.)

The HCV genome consists of a single strand RNA about 9.5 kb encoding a precursor polyprotein of about 3000 amino acids. (Choo et al., *Science* 244:362-364, 1989, Choo et al., *Science* 244:359-362, 1989.) The HCV polyprotein contains the viral proteins in the order: C-E1-E2-p7-NS2-NS3-NS4A-NS4B-NS5A-NS5B. Cleavage of the precursor polyprotein results in mature structural and non-structural viral proteins. (Neddermann et al., *Biol. Chem.* 378:469-476, 1997.)

As part of its infection cycle, HCV enters into a cell. Host cell LDL receptors and CD81 molecules have been identified as putative HCV receptors. The LDL receptor has been suggested to mediate virus internalization via binding to LDL particles that are virus-associated. (Agnello et al., *Proc. Natl. Acad. Sci. U.S.A.* 96:12766-12771, 1999.) The CD81 molecule has been suggested to bind HCV E2 based on recombinant envelope protein E2 from HCV genotype 1a. (Pileri et al., *Science* 282:938-941, 1998.)

HCV envelope glycoprotein E2 was found to bind human hepatoma cells independently of CD81. The receptor responsible for E2 binding to human hepatic cells was identified as the human scavenger receptor class B type I (SR-B1). (Scarselli et al., *The EMBO Journal* 21:5017-5025, 2002.)

SUMMARY OF THE INVENTION

The present invention features antigen binding protein that bind to a SR-BI target region identified herein as a region involved in HCV E2 binding. Identified target regions are regions bound by a single-chain antibody of SEQ ID NOs: 1, 2, 3 or 4.

Thus, a first aspect of the present invention features an isolated antigen binding protein comprising a first variable region and a second variable region. The first and second variable regions bind one or more target regions selected from the group consisting of: the SEQ ID NO: 1 target region, the SEQ ID NO: 2 target region, the SEQ ID NO: 3 target region, and the SEQ ID NO: 4 target region.

Reference to "isolated" indicates a different form than found in nature. The different form can be, for example, a different purity than found in nature and/or a structure that is not found in nature. A structure not found in nature includes recombinant structures where different regions are combined together, for example, humanized antibodies where one or more murine CDR is inserted onto a human framework scaffold, hybrid antibodies where one or more CDR from an antibody binding protein is inserted into a different framework scaffold, and antibodies derived from natural human sequences where genes coding light and heavy variable domains were randomly combined together.

The isolated protein is preferably substantially free of serum proteins. A protein substantially free of serum proteins is present in an environment lacking most or all serum proteins.

A "variable region" has the structure of an antibody variable region from a heavy or light chain. Antibody heavy and light chain variable regions contain three complementary determining regions interspaced onto a framework. The complementary determining regions are primarily responsible for recognizing a particular epitope.

A target region defined with respect to SEQ ID NOs: 1, 2, 3 or 4, is an SR-B1 region to which the corresponding single-chain antibody binds. For example, the SEQ ID NO: 1 target region is a region to which a polypeptide of SEQ ID NO: 1 binds.

A protein binding to same target region as an identified target region competes with either SEQ ID NOs: 1, 2, 3 or 4 for binding to the identified target region. For example, a protein that competes with a polypeptide of SEQ ID NO: 1 for binding to SR-BI binds to the SEQ ID NO: 1 target region.

Reference to "protein" or "polypeptide" indicates a contiguous amino acid sequence and does not provide a minimum or maximum size limitation. One or more amino acids present in the protein or polypeptide may contain a post-translational modification, such as glycosylation and disulfide bond formation.

A preferred antigen binding protein is a monoclonal antibody. Reference to a "monoclonal antibody" indicates a collection of antibodies having the same, or substantially the same, complementary determining region, and binding specificity. The variation in the monoclonal antibodies is that which would occur if the antibodies were produced from the same construct(s).

Monoclonal antibodies can be produced, for example, from a particular hybridoma and from a recombinant cell containing one or more recombinant genes encoding the antibody. The antibody may be encoded by more than one recombinant gene where, for example, one gene encodes the heavy chain and one gene encodes the light chain.

Another aspect of the present invention describes a pharmaceutical composition. The composition contains an antigen binding protein and a pharmaceutically acceptable carrier.

Another aspect of the present invention describes a nucleic acid containing a recombinant gene encoding an antigen binding protein. A recombinant gene contains recombinant nucleic acid encoding a polypeptide along with regulatory elements for proper transcription and processing (which may include translational and post translational elements). The recombinant gene can exist independent of a host genome or can be part of a host genome.

A recombinant nucleic acid is nucleic acid that by virtue of its sequence and/or form does not occur in nature. Examples of recombinant nucleic acid include purified nucleic acid, two or more nucleic acid regions combined together providing a different nucleic acid than found in nature, and the absence of one or more nucleic acid regions (e.g., upstream or downstream regions) that are naturally associated with each other.

Another aspect of the present invention describes a method of inhibiting HCV replication in cell. The method involves providing to the cell an effective amount of an antigen binding protein.

Another aspect of the present invention describes a method of inhibiting HCV replication in a patient. The method involves administering to the patient an effective amount of an antigen binding protein.

Another aspect of the present invention describes a recombinant cell comprising a recombinant nucleic acid encoding an antigen binding protein.

Another aspect of the present invention describes a method of producing an antigen binding protein. The method involves growing a cell comprising a recombinant gene encoding an antigen binding under conditions where the nucleotide sequence is expressed in the cell and isolating the antigen binding protein.

Reference to "isolating" indicates separation of the protein from one or more cellular components. Preferably, the protein is substantially purified.

Unless particular terms are mutually exclusive, reference to "or" indicates either or both possibilities. Occasionally phrases such as "and/or" are used to highlight either or both possibilities.

Reference to open-ended terms such as "comprises" allows for additional elements or steps. Occasionally phrases such as "one or more" are used with or without open-ended terms to highlight the possibility of additional elements or steps.

Unless explicitly stated reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIGS. 3A and 3B provide an amino acid sequence alignment of single-chain antibodies of SEQ ID NOs: 1, 2, 3, and 4, and indicates the different complementary determining regions ("CDR"), framework regions ("FW") and linker. "SEQ 1" refers to SEQ ID NO: 1. "SEQ 2" refers to SEQ ID NO: 2. "SEQ 3" refers to SEQ ID NO: 3. "SEQ 4" refers to SEQ ID NO: 4. The CDR's can be longer than illustrated in the figure. The provided alignment eliminates common gaps in the CDR's.

FIGS. 4A-4D illustrate nucleic acid sequences encoding SEQ ID NOs: 1, 2, 3 and 4. FIG. 4A illustrates a nucleic acid sequence (SEQ ID NO: 5) encoding SEQ ID NO: 1. FIG. 4B illustrates a nucleic acid sequence (SEQ ID NO: 6) encoding SEQ ID NO: 2. FIG. 4C illustrates a nucleic acid sequence (SEQ ID NO: 7) encoding SEQ ID NO: 3. FIG. 4D illustrates a nucleic acid sequence (SEQ ID NO: 8) encoding SEQ ID NO: 4.

FIG. 5 provides the amino acid sequence of SEQ ID NO: 9.

DETAILED DESCRIPTION OF THE INVENTION

The present application identifies particular SR-BI regions that can be targeted to inhibit HCV E2 binding to a cell. The examples provided below illustrate that ability of single-chain antibodies of SEQ ID NOs: 1-4 to inhibit HCV E2 binding, the ability of IgG molecules containing SEQ ID NOs: 2 or 4 variable region to inhibit HCV E2 binding, and the ability of SEQ ID NO: 2 to inhibit HCV replication.

Inhibiting HCV E2 binding can have research tool and therapeutic applications. Research tool applications include using the binding protein as a tool to study HCV binding and replication, and to identify additional binding protein that bind to the same region. Therapeutic applications include using those compounds having appropriate pharmacological properties such as efficacy and lack of unacceptable toxicity to treat, or inhibit onset of, HCV in a patient.

The target SR-B1 is a glycoprotein containing a large extracellular loop anchored to the plasma membrane at both the amino and carboxyl termini by transmembrane domains. (Krieger *Journal of Clinical Investigation* 108:793-797, 2001.) SR-BI is highly expressed in the liver hepatocytes and steroidogenic tissues, and mediates the selective cellular uptake of cholesterol and phospholipids. (Acton et al., *Science* 271:518-520, 1996, Urban et al., *J. Biol. Chem.* 275: 33409-33415, 2000.)

SEQ ID NO: 9 provides the amino acid sequence of SR-B1 used to obtain single-chain antibodies of SEQ ID NOs 1, 2, 3, and 4. SEQ ID NO: 9 can be used a frame of reference for antigen binding protein.

I. ANTIGEN BINDING PROTEIN

Antigen binding proteins contain antibody variable regions providing for specific binding to an epitope. The antibody variable region can be present in, for example, a complete antibody, an antibody fragment, and a recombinant derivative of an antibody or antibody fragment.

Figure 1:
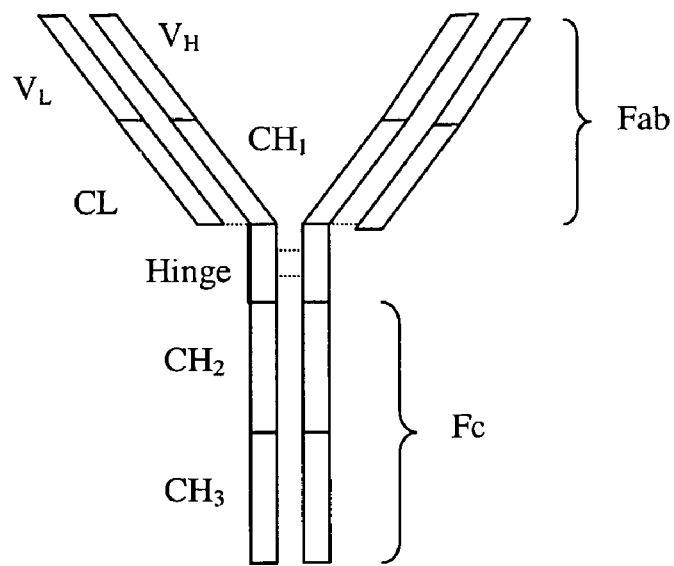
FIG. 1 illustrates the structure of an IgG molecule. "$V_L$" refers to a light chain variable region. "$V_H$" refers to a heavy chain variable region. "CL" refers to a light chain constant region. "$CH_1$", "$CH_2$" and "$CH_3$" are heavy chain constant regions.
Figure 2:
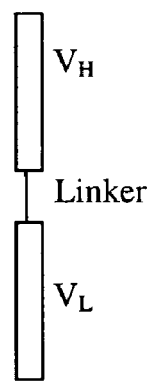
FIG. 2 illustrates the structure of a single-chain antibody. "$V_L$" refers to a light chain variable region. "$V_H$" refers to a heavy chain variable region.

FIGS. 1 and 2 provide some examples of different types of antigen binding proteins. FIG. 1 illustrates a complete IgG molecule and different antibody regions. An IgG molecule contains four polypeptide chains: two longer length heavy chains and two shorter light chains. Heavy and light chains each contain a constant region and a variable region. Within the variable regions are hypervariable regions responsible for antigen specificity. (See, for example, Breitling et al., Recombinant Antibodies, John Wiley & Sons, Inc. and Spektrum Akademischer Verlag, 1999; and Lewin, Genes IV, Oxford University Press and Cell Press, 1990.)

The two heavy chain carboxyl regions are constant regions joined by disulfide binding to produce an Fc region. The Fc region is important for providing biological activity such as complement and macrophage activation. Each of the two heavy chain polypeptides making up the Fc region extend into different Fab regions through a hinge region.

In higher vertebrates there are two classes of light chains and five classes of heavy chains. The light chains are either κ or λ. The heavy chains define the antibody class and are either α, δ, ε, γ, or μ. For example, IgG has a γ heavy chain. Subclasses also exist for different types of heavy chains such as $\gamma_1$, $\gamma_2$, $\gamma_3$, and $\gamma_4$. Heavy chains impart a distinctive conformation to hinge and tail regions. (Lewin, Genes IV, Oxford University Press and Cell Press, 1990.)

Subclasses can be further characterized. For example, $IgG_2$ subtypes can be further divided into $IgG_{2a}$ and $IgG_{2b}$. (Hahn G. S. (1982) Antibody Structure, Function and Active Sites. In *Physiology of Immunoglobulins: Diagnostic and Clinical Aspects*. S. E. Ritzmann (ed) Alan Liss Inc., New York; and Turner M. W. (1983) Immunoglobulins. In *Immunology in Medicine. A Comprehensive Guide to Clinical Immunology*. $2^{nd}$ Edition. E. J. Holborow & W. G. Reeves (eds.) Grune & Stratton, London.)

Antibody fragments containing an antibody variable region include Fv, Fab, and $Fab_2$ regions. Each Fab region contains a light chain made up of a variable region and a constant region, and a heavy chain region containing a variable region and a constant region. A light chain is joined to a heavy chain by disulfide bonding through constant regions. The light and heavy chain variable regions of a Fab region provide for an Fv region that participates in antigen binding.

The antibody variable region can also be part of protein containing variable regions such as single chain antibody and a minibody. A single chain antibody contains a light and a heavy variable region joined together by a linker. (See FIG. 2.) The linker can be, for example, about 5 to 16 amino acids. A minibody is a single chain-CH3 fusion protein that self assembles into a bivalent dimer of about 80 kDa.

Specificity of the variable region is determined by three hypervariable regions (also referred to as complementarity determining regions), that are interposed between more conserved flanking regions (also referred to as framework regions). Amino acids associated with framework regions and complementarity determining regions can be numbered and aligned as described by Kabat et al., Sequences of Proteins of Immunological Interest, U.S. Department of Health and Human Services, 1991.

II. SEQ ID NOS: 1-4 TARGETED REGIONS

The SR-BI regions bound by SEQ ID NOs: 1, 2, 3 and/or 4 provide target regions for inhibiting HCV E2 binding. Single-chain antibodies of SEQ ID NOs: 1-4 do not necessarily bind to different regions. SEQ ID NOs: 1 and 4 should recognize the same epitope. SEQ ID NOs: 1 and 4 have a very high homology with one different amino acid in CDR3 and a few minor changes in the framework regions.

Antigen binding protein described herein binds to a SR-BI target region involved in HCV E2 binding. While inhibition of HCV E2 binding is expected to occur by interacting with a site directly involved with HCV E2 binding, a region involved in HCV E2 binding can include regions not directly interacting with HCV E2 binding. For example, the targeted region may be involved in providing a proper conformation for a different region which directly binds to HCV E2.

Single-chain antibodies of SEQ ID NOs: 1-4 are examples of antigen binding proteins that can be used to inhibit HCV E2 binding. SEQ ID NOs: 1-4 can also be used to design additional antigen-binding proteins that bind to a targeted region. The design of additional binding protein can be performed, for example, using techniques involving derivatizing SEQ ID NOs: 1-4, using of the sequence information provided in SEQ ID NOs: 1-4, or employing SEQ ID NOs: 1-4 as tool to experimentally identify protein that bind to the same region.

SEQ ID NOs: 1-4 provide variable region sequences and complementary determining region sequences that can be incorporated into an antigen binding protein. FIGS. 3A and 3B provide the amino acid sequence of SEQ ID NOs: 1-4 and indicate the location of different complementary determining regions, frame work regions, and a linker region.

The ability of antigen binding protein to inhibit HCV E2 binding and HCV replication can be evaluated using methods such as those described in the Examples Infra. An antigen binding protein inhibiting HCV E2 binding can be used as a starting construct to obtain additional antigen binding protein.

II.A. Single-Chain Antibody Modification

Single-chain antibodies of a known sequence, such as SEQ ID NOs: 1, 2, 3 or 4, can be derivatized to enhance stability and to enhance antigen binding. Factors effecting stability include exposure of hydrophobic residues that are hidden at the interface of a whole Ig molecule at the constant domain interface; hydrophobic region exposure on the Fv surface leading to intermolecular interaction; and hydrophilic residues in the interior of the Fv beta sheet or at the normally interface between $V_H$ and $V_L$. (Chowdhury et al., Engineering scFvs for Improved Stability, p. 237-254 in Recombinant Antibodies for Cancer Therapy Methods and Protocols, (Eds. Welschof and Krauss) Humana Press, Totowa, N.J., 2003.)

Stability can be enhanced by substituting problematic residues impacting on stability. Buried hydrophobic residue and exposed hydrophobic residues are potentially problematic. Techniques for enhancing single chain antibody stability taking into account problematic residue are well known in art. (Chowdhury et al., Engineering scFvs for Improved Stability, p. 237-254 in Recombinant Antibodies for Cancer Therapy Methods and Protocols, (Eds. Welschof and Krauss) Humana Press, Totowa, N.J., 2003.)

Single chain antigen affinity can be enhanced using techniques such as site directed mutagenesis and chain shuffling. Site directed mutagenesis can be performed to substitute one or more complementary determining region amino acids and then identifying antibodies with higher affinity. (Azzazy et al., *Clinical Biochemistry* 35:425-445, 2002.)

Chain shuffling can be preformed to provide new combinations of variable regions binding to an antigen. Chain shuffling can be performed by combining a single chain antibody variable region (e.g., $V_H$) with a repertoire of different variable region (e.g., $V_L$'s) to produce a single chain antibody library. The resulting library contains a variable region known to be specific for the antigen and a random variable region.

The library can be panned against the antigen to identify single-chain antibodies binding to the antigen with enhanced affinity.

II.B. Antigen Binding Protein Construction Based on Variable Region Information

Variable regions and complementary determining regions from single-chain antibodies of SEQ ID NOs: 1-4 can be incorporated into antigen binding proteins. Techniques for incorporating a variable region into an antibody or an antibody fragment are well known in the art. (E.g., Azzazy et al., *Clinical Biochemistry* 35:425-445, 2002, Persic et al., *Gene* 187:9-18, 1997.) An example of such a technique is as follows:

1) Separately amplify the Fv domains using PCR primers specific for the $V_H$ and $V_L$ regions, the primers can include additional nucleotides for introducing unique restriction sites, for providing splice sites, and encoding additional amino acids;

2) Incorporate the amplified variable encoding regions into mammalian expression cassettes. $V_H$ encoding nucleic acid can be inserted into a plasmid containing a cassette for expressing a human heavy (e.g., human gamma 4 heavy chain), while the $V_L$ encoding region can be introduced into a vector expressing a light chain (e.g., human lambda light chain). Both vectors should carry an intron between the leader sequence and the constant region sequence of the antibody. The intron should contain unique restriction sites suitable for cloning the amplified FV domains; and 3) IgG production can be achieved by co-transfecting the $V_H$ and $V_L$ expression vector in 293-EBNA.

Numerous variations of the outlined procedure can be performed to incorporate a variable region into an antibody or an antibody fragment. Such variations include, for example, using a vector encoding different types of antibody light and heavy chains or fragments thereof, using a single vector, and using different types of host cells.

Technique for grafting complementary determining regions into an antibody or antibody fragment are also well known in art. Such techniques are generally described with reference to humanizing murine antibodies by grafting murine variable regions onto a human antibody framework and, if needed making further modifications. (E.g., O'Brien et al., Humanization of Monoclonal Antibodies by CDR Grafting, p 81-100, From *Methods* in Molecular Biology Vol 207: Recombinant antibodies for Cancer Therapy: Methods and Protocols (Eds Welschof and Krauss) Humana Press, Totowa, N.J., 2003.)

In different embodiments the antigen binding protein is a complete antibody, an antibody fragment, or a recombinant derivative of an antibody or antibody fragment, wherein;

a) the first variable region is a $V_h$ region comprising a first CDR comprising amino acids 31-35 of SEQ ID NO: 1, a second CDR comprising amino acids 50-66 of SEQ ID NO: 1, and a third CDR comprising amino acids 99-108 of SEQ ID NO: 1; and the second variable region is a $V_l$ region comprising a first CDR comprising amino acids 158-170 of SEQ ID NO: 1, a second CDR comprising amino acids 186-192 of SEQ ID NO: 1, and a third CDR comprising amino acids 225-235 of SEQ ID NO: 1;

b) the first variable region is a $V_h$ region comprising a first CDR comprising amino acids 31-37 of SEQ ID NO: 2, a second CDR comprising amino acids 52-67 of SEQ ID NO: 2, and a third CDR comprising amino acids 100-114 of SEQ ID NO: 2; and the second variable region is a $V_l$ region comprising a first CDR comprising amino acids 164-176 of SEQ ID NO: 2, a second CDR comprising amino acids 192-198 of SEQ ID NO: 2, and a third CDR comprising amino acids 231-241 of SEQ ID NO: 2;

c) the first variable region is a $V_h$ region comprising a first CDR comprising amino acids 31-35 of SEQ ID NO: 3, a second CDR comprising amino acids 50-66 of SEQ ID NO: 3, and a third CDR comprising amino acids 99-108 of SEQ ID NO: 3; and the second variable region is a $V_l$ region comprising a first CDR comprising amino acids 158-170 of SEQ ID NO: 3, a second CDR comprising amino acids 186-192 of SEQ ID NO: 3, and a third CDR comprising amino acids 225-235 of SEQ ID NO: 3;

d) the first variable region is a $V_h$ region comprising a first CDR comprising amino acids 31-35 of SEQ ID NO: 4, a second CDR comprising amino acids 50-66 of SEQ ID NO: 4, and a third CDR comprising amino acids 99-108 of SEQ ID NO: 4; and the second variable region is a $V_l$ region comprising a first CDR comprising amino acids 158-170 of SEQ ID NO: 4, a second CDR comprising amino acids 186-192 of SEQ ID NO: 4, and a third CDR comprising amino acids 225-235 of SEQ ID NO: 4;

e) the first variable region consists of amino acids 1-119 of SEQ ID NO: 1 and the second variable region consists of amino acids 136-245 of SEQ ID NO: 1;

f) the first variable region consists of amino acids 1-125 of SEQ ID NO: 2 and the second variable region consists of amino acids 142-251 of SEQ ID NO: 2;

g) the first variable region consists of amino acids 1-119 of SEQ ID NO: 3 and the second variable region consists of amino acids 136-245 of SEQ ID NO: 3; or h) the first variable region consists of amino acids 1-119 of SEQ ID NO: 4 and the second variable region consists of amino acids 136-245 of SEQ ID NO: 4.

II.C. Further Identification of Antigen Binding Proteins

Single-chain antibodies SEQ ID NOs: 1, 2, 3 or 4 can be used to identify additional antigen binding proteins binding to a targeted region. Identification can be performed using different techniques such as screening for antigen binding proteins that compete with SEQ ID NOs: 1, 2, 3 or 4 binding to SR-B1, mapping the epitope recognized by single-chain antibodies SEQ ID NOs: 1, 2, 3 or 4, and utilizing the epitope itself to select for additional antigen binding protein.

Antigen binding proteins for use in a competition assay can be generated using SR-B1 as an antigen. Techniques for generating antigen binding protein such as a single-chain antibody, an antibody, or an antibody fragment are well known in the art. Examples of such techniques include the use of phage display technology, identification and humanization of rodent antibodies, and generation of human antibodies using a XenoMouse or Trans-Chromo mouse. (E.g., Azzazy et al., *Clinical Biochemistry* 35:425-445, 2002, Berger et al., *Am. J. Med. Sci.* 324(1): 14-40, 2002.)

III. PROTEIN PRODUCTION

Antigen binding protein are preferably produced using recombinant nucleic acid techniques or through the use of a hybridoma. Recombinant nucleic acid techniques involve constructing a nucleic acid template for protein synthesis. A hybridoma is an immortalized cell line producing the antigen binding protein.

Recombinant nucleic acid encoding an antigen binding protein can be expressed in a host cell that in effect serves as a factory for the encoded protein. The recombinant nucleic acid can provide a recombinant gene encoding the antigen binding protein that exists autonomously from a host cell genome or as part of the host cell genome.

A recombinant gene contains nucleic acid encoding a protein along with regulatory elements for protein expression. Generally, the regulatory elements that are present in a recombinant gene include a transcriptional promoter, a ribosome binding site, a terminator, and an optionally present operator. A preferred element for processing in eukaryotic cells is a polyadenylation signal. Antibody associated introns may also be present. Examples of expression cassettes for antibody or antibody fragment production are well known in art. (E.g., Persic et al., *Gene* 187:9-18, 1997, Boel et al., *J. Immunol. Methods* 239:153-166, 2000, Liang et al., *J. Immunol. Methods* 247:119-130, 2001.)

Expression of a recombinant gene in a cell is facilitated using an expression vector. Preferably, an expression vector, in addition to a recombinant gene, also contains an origin of replication for autonomous replication in a host cell, a selectable marker, a limited number of useful restriction enzyme sites, and a potential for high copy number. Examples of expression vectors for antibody and antibody fragment production are well known in art. (E.g., Persic et al., *Gene* 187: 9-18, 1997, Boel et al., *J. Immunol. Methods* 239:153-166, 2000, Liang et al., *J. Immunol. Methods* 247:119-130, 2001.)

If desired, nucleic acid encoding an antibody may be integrated into the host chromosome using techniques well known in the art. (See, Ausubel, *Current Protocols in Molecular Biology*, John Wiley, 1987-1998, Marks et al., International Application Number WO 95/17516, International Publication Date Jun. 29, 1995.)

A variety of different cell lines can be used for recombinant antigen binding protein expression, including those from prokaryotic organisms (e.g., *E. coli, Bacillus,* and *Streptomyces*) and from Eukaryotic (e.g., yeast, Baculovirus, and mammalian). (Breitling et al., Recombinant Antibodies, John Wiley & Sons, Inc. and Spektrum Akademischer Verlag, 1999.)

Preferred hosts for recombinant antigen binding protein expression are mammalian cells able to produce antigen binding protein with proper post translational modifications. Post translational modifications include disulfide bond formation and glycosylation. Another type of post translational modification is signal peptide cleavage.

Proper glycosylation can be important for antibody function. (Yoo et al., *Journal of Immunological Methods* 261:1-20, 2002.) Naturally occurring antibodies contain at least one N-linked carbohydrate attached to a heavy chain. (Id.) Additional N-linked carbohydrates and O-linked carbohydrates may be present and may be important for antibody function. (Id.)

Different types of mammalian host cells can be used to provide for efficient post-translational modifications. Examples of such host cells include Chinese hamster ovary (Cho), HeLa, C6, PC12, and myeloma cells. (Yoo et al., *Journal of Immunological Methods* 261:1-20, 2002, Persic et al., *Gene* 187:9-18, 1997.)

A hybridoma is an immortalized antibody producing cell line. A hybridoma can be produced using techniques such as those described in Ausubel *Current Protocols in Molecular Biology, John Wiley,* 1987-1998, Harlow et al., *Antibodies, A Laboratory Manual*, Cold Spring Harbor Laboratory, 1988, and Kohler et al., *Nature* 256, 495-497, 1975.

IV. COMBINATION TREATMENT

Antigen binding protein that bind to suitable SR-BI sites can be used to inhibit HCV and treat HCV patients by itself, or in combination with one or more other anti-HCV agents. Currently approved anti-HCV agents are interferon alpha, and interferon alpha in combination with ribovarin. Different forms of interferon alpha, such as recombinant interferon and peglyated interferons, can used to treat HCV infections. (De Francesco et al., *Antiviral Research* 58:1-16, 2003, Walker et al., *Antiviral Chemistry & Chemotherapy* 14:1-21, 2003.)

A variety of different anti-HCV agents are in different phases of clinical developments. The different anti-HCV agents being developed include agents directed against different HCV targets. Examples of different HCV targets include HCV polymerase and HCV NS3-NS4A protease. (De Francesco et al., *Antiviral Research* 58:1-16, 2003, Walker et al., *Antiviral Chemistry & Chemotherapy* 14:1-21, 2003.)

V. ADMINISTRATION

Guidelines for pharmaceutical administration in general are provided in, for example, *Remington's Pharmaceutical Sciences* 20$^{th}$ Edition, Ed. Gennaro, Mack Publishing, 2000; and *Modern Pharmaceutics* 2$^{nd}$ Edition, Eds. Banker and Rhodes, Marcel Dekker, Inc., 1990.

Pharmaceutically acceptable carriers facilitate storage or administration of an antigen binding protein. Substances used to stabilize protein solution formulations include carbohydrates, amino acids, and buffering salts. (Middaugh et al., Handbook of Experimental Pharmacology 137:33-58, 1999.)

Antigen binding proteins can be administered by different routes such as subcutaneous, intramuscular, or mucosal. Subcutaneous and intramuscular administration can be performed using, for example, needles or jet-injectors. Mucosal delivery, such as nasal delivery, can involve using enhancers or mucoadhesives to produce a longer retention time at adsorption sites. (Middaugh et al., *Handbook of Experimental Pharmacology* 137:33-58, 1999.)

Suitable dosing regimens are preferably determined taking into account factors well known in the art including age, weight, sex and medical condition of the patient; the route of administration; the desired effect; and the particular compound employed. It is expected that a dose would consist of the range of 1.0 μg to 1.0 mg total protein, in different embodiments of the present invention the range is 0.01 mg to 1.0 mg and 0.1 mg to 1.0 mg.

VI. EXAMPLES

Examples are provided below further illustrating different features of the present invention. The examples also illustrate useful methodology for practicing the invention. These examples do not limit the claimed invention.

Example 1

Experimental Procedure to Obtain SR-B1-Specific Phage Antibodies

The CAT (Cambridge antibody technology) phage library CS was screened for single-chain antibodies binding to SR-B1. The library provides single-chain antibodies containing a variable portion of heavy chain and light chain antibodies exposed on the surface of a filamentous phage as a fusion to the N terminus of the pIII protein. The $V_H$ region is joined to the $V_L$ region by a linker of Ser and Gly.

To select phage displaying antibodies specifically binding to the SR-B1 receptor, whole cells were utilized for phage enrichment. The library ($10^{11}$ phage) was pre-incubated with $10^7$ CHO cells for 1 hour at room temperature, followed by centrifugation. The unbound phage present in the supernatant were recovered and incubated for 1 hour with CHO cells stably expressing the human SR-B1 receptor (SEQ ID NO: 9). Cells were then washed several times with PBS and resuspended in elution buffer (triethylamina, 100 mM) for 25 minutes, followed by adjustment of the pH with Tris.HCl. Recovered phage were amplified by infecting TG1 cells and subjected to other two rounds of selection as described above.

Following the third round of selection, $3 \times 10^5$ phage were recovered. A sample of these (144 phage) was tested in a cell based ELISA, using SR-B1 expressing CHO cells, in parallel with CHO cells as negative control. Among these 11 phage clones were scored as SR-B1-specific. Clones were subsequently tested for the ability to HCV E2 binding.

Example 2

Inhibition of HCV E2

Clones encoding SEQ ID NOs: 1, 2, 3 and 4 produced outside the phage context were able to inhibit the binding of the HCV E2 protein to HepG2 cells. HepG2 is a human hepatoma cell line.

Cells were detached and washed in phosphate buffered saline (PBS), 0.2% BSA, 10 mM Hepes (washing buffer). $4 \times 10^5$ cells were allowed to bind to different concentrations (0.5-5-20-40 µg/ml) of single chain antibodies or an unrelated single chain control D5 at room temperature for 30 minutes. Cells were then incubated for 1 hour at room temperature with recombinant soluble E2. Binding was revealed by anti-E2 rat mAb 6/1a (Patel et al. *J. Gen. Virol.* 81:2873-2883, 2000) and a secondary anti-rat PE-conjugated mAb. Fluorescence associated to the cells was measured by FACS analysis.

Figure 6:
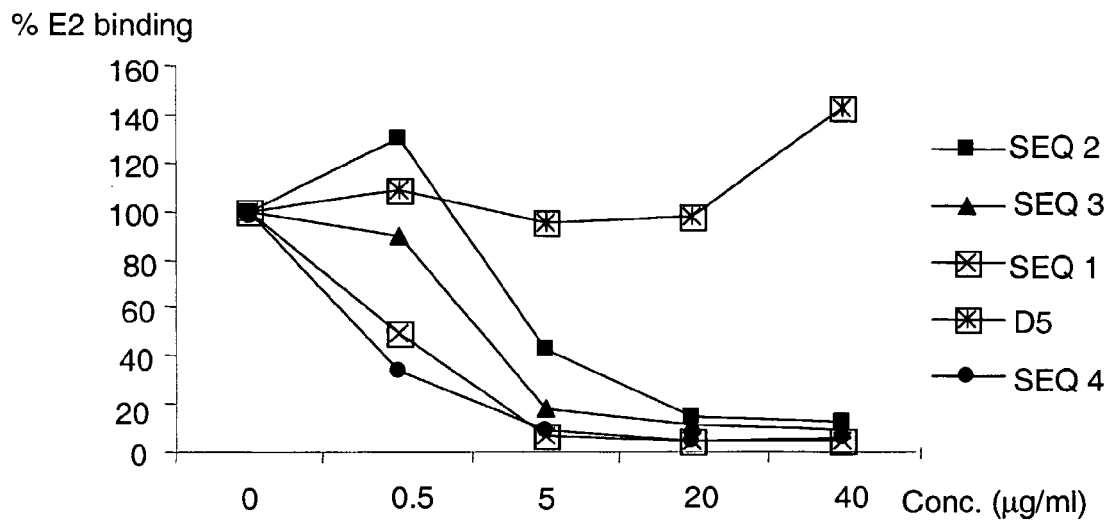
FIG. 6 provides results illustrating the ability of single-chain antibodies of SEQ ID NOs: 1, 2 3, and 4 to inhibit E2 protein binding to the HepG2 cell line. The vertical axis represents the percentage of E2 protein binding to HepG2 cells, referring to cells not pre-incubated with single-chain antibodies. As a control, an unrelated single-chain antibody was used (D5). The experiment was performed in duplicate, the averages of the duplicate samples are shown.

As shown in FIG. 6, anti-SRB1 single-chain antibodies of SEQ ID NOs: 1, 2, 3, and 4 inhibited E2 protein binding to the HepG2 cell line. The vertical axis represents the percentage of E2 protein binding to HepG2 cells, referring to cells not pre-incubated with antibodies. The experiment was performed in duplicate, the averages of the duplicate samples are shown.

Example 3

Inhibition of HCV Infection Using the Single-Chain Antibody of SEQ ID NO: 2

The ability of single-chain antibodies able to inhibit HCV E2 binding to also inhibit HCV replication was illustrated using the single-chain antibody of SEQ ID NO: 2.

Isolated human hepatocytes from surgical liver resection were seeded in 24 well microplates at the density of $3 \times 10^5$ cells/well. Cells were allowed to attach and recover 24 hours and then medium was replaced with fresh one containing different concentrations of anti-SRB1 single-chain antibody SEQ ID NO: 2 (25 and 5 µg/ml) or a control unrelated single chain antibody FV at the highest concentration (25 µg/ml).

Hepatocytes were preincubated 1 hour at 37° C. with the indicated amounts of single-chain antibodies, then medium was replaced with fresh one containing the same amounts of single-chain antibodies and a fixed amount (100 µl) of an infectious human serum from a HCV chronic patient. Cells were incubated 18 hours with the virus to allow infection, then washed and incubated for four days. Total RNA was extracted and viral replication was measured by quantitative RT-PCR.

Figure 7:
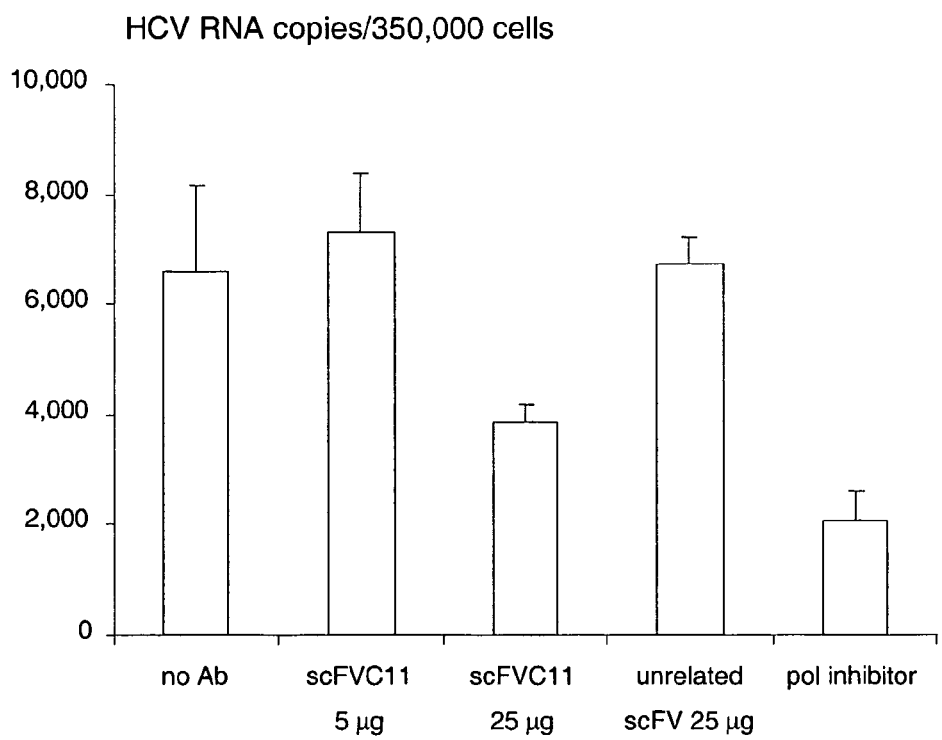
FIG. 7 provides results illustrating the inhibition of HCV infection of cultured human hepatocytes by the single-chain antibody of SEQ ID NO: 2 ("scFVC11"). Viral replication was measured on total RNA by quantitative PCR and expressed as number of HCV copies/350000 cells. The experiment was performed in triplicate wells and values are shown with standard deviations. Single-chain antibody of SEQ ID NO: 2 was tested at two different concentrations: 25 and 5 µg/ml. As a control, an unrelated single-chain antibody was used (FV) at the concentration of 25 µg/ml. As a positive control of inhibition of infection, a HCV replicase inhibitor was used ("Pol inhibitor").

Typically, $10^4$ to $10^5$ copies of genomes/well are detected after four days from infection. To be sure that the measured viral RNA derived from active replication, a small molecule inhibitor of the viral replicase was included as a positive control. As shown in FIG. 7, anti-SRB1 single chain of SEQ ID NO: 2 (scFVC11) can block HCV infection of cultured human hepatocytes.

Example 4

IgG Production from Single-Chain Antibodies

IgG4 molecules were produced containing SEQ ID NO: 2 or SEQ ID NO: 4 variable regions. SEQ ID NOs: 2 or 4 variable regions were separately amplified by PCR using primers specific for the $V_H$ and the $V_L$ regions. The primers contained additional nucleotides for the introduction of unique restriction sites, and bases representing splice sites or coding for additional amino acids.

The amplified products were introduced into two separate mammalian expression vectors: $V_H$ was inserted in the pEU8.2 containing a cassette for the expression of human gamma 4 heavy chain, while $V_L$ was introduced into the vector pEU 4.2 expressing the constant region of the human lambda light chain. Both vectors carry an intron between the leader sequence and the constant region sequence of the antibody. The intron contains unique restriction sites suitable for cloning the amplified variable domains.

IgG production was achieved by co-transfecting the $V_H$ and $V_L$ expression vectors into 293-EBNA cells (Invitrogen), using Lipofectamine 2000 reagent (Invitrogen) and collecting the supernatant for up to eight days. IgG's were purified from culture medium using Hi-Trap protein A columns, Amersham, following manufacturers instruction.

Example 5

Inhibition of HCV E2 Protein Binding Using Anti-SRB1 IgG

Cho7s cells stably expressing the human SR-B1 receptor (Scarselli et al., *The EMBO Journal* 21(19):5017-5025, 2002) were used to evaluate the ability of anti-SRB1 IgG containing the SEQ ID NO: 2 or 4 variable regions to inhibit HCV E2 binding. Cells were detached and washed in phosphate buffered saline (PBS), 0.2% BSA, 10 mM Hepes (washing buffer). $4 \times 10^5$ cells were allowed to bind to different concentrations (60-12-2.4 µg/ml) of antibodies at room temperature for 30 minutes. Cells were then incubated for 1 hour at room temperature with recombinant soluble E2 (carrying a His-Tag).

Figure 8:
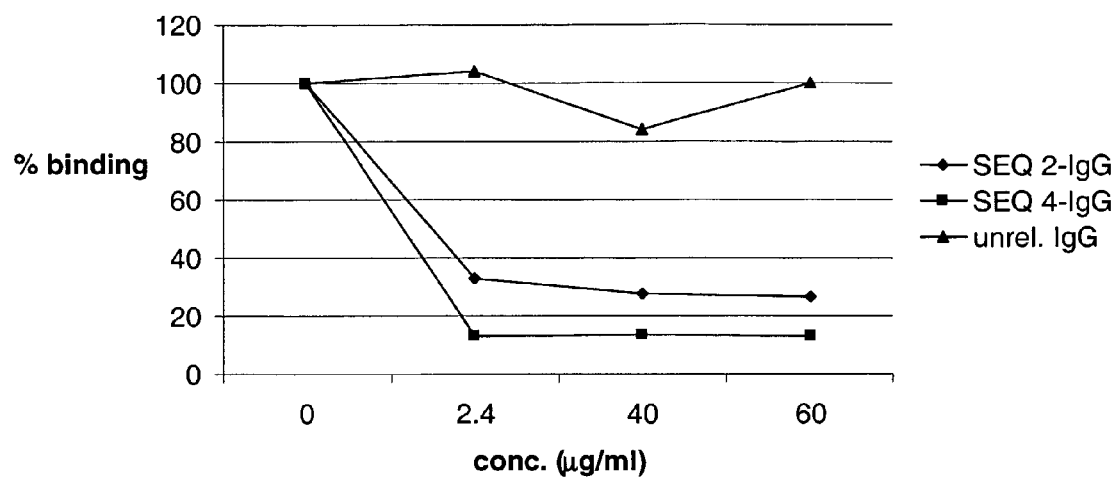
FIG. 8 provides results illustrating the ability of IgG4 molecules containing SEQ ID NO: 2 or SEQ ID NO: 4 variable regions to inhibit E2 protein binding to the CHO7s cell line. An unrelated IgG was used as a negative control.

Binding was revealed by an anti-penta His biotin conjugate and streptavidin-R-PE. Fluorescence associated to the cells was measured by FACS analysis. As shown in FIG. 8, anti-SRB1 IgG4 SEQ ID NOs: 2 and 4 inhibit E2 protein binding to the Cho7s cell line. Unrelated IgGs were used as a negative control.

Other embodiments are within the following claims. While several embodiments have been shown and described, various modifications may be made without departing from the spirit and scope of the present invention.

What is claimed is:

1. An antibody or antigen binding fragment thereof that comprises a first variable region and a second variable region, wherein either:
   a) said first variable region is a $V_h$ region comprising a first CDR comprising amino acids 31-35 of SEQ ID NO: 1, a second CDR comprising amino acids 50-66 of SEQ ID NO: 1, and a third CDR comprising amino acids 99-108 of SEQ ID NO: 1; and said second variable region is a $V_1$ region comprising a first CDR comprising amino acids 158-170 of SEQ ID NO: 1, a second CDR comprising amino acids 186-192 of SEQ ID NO: 1, and a third CDR comprising amino acids 225-235 of SEQ ID NO: 1;
   b) said first variable region is a $V_h$ region comprising a first CDR comprising amino acids 31-37 of SEQ ID NO: 2, a second CDR comprising amino acids 52-67 of SEQ ID NO: 2, and a third CDR comprising the amino acids 100-114 of SEQ ID NO: 2; and said second variable region is a $V_1$ region comprising a first CDR comprising amino acids 164-176 of SEQ ID NO: 2, a second CDR comprising amino acids 192-198 of SEQ ID NO: 2, and a third CDR comprising amino acids 231-241 of SEQ ID NO: 2;
   c) said first variable region is a $V_h$ region comprising a first CDR comprising amino acids 31-35 of SEQ ID NO: 3, a second CDR comprising amino acids 50-66 of SEQ ID NO: 3, and a third CDR comprising amino acids 99-108 of SEQ ID NO: 3; and said second variable region is a $V_1$ region comprising a first CDR comprising amino acids 158-170 of SEQ ID NO: 3, a second CDR comprising amino acids 186-192 of SEQ ID NO: 3, and a third CDR comprising amino acids 225-235 of SEQ ID NO: 3; or
   d) said first variable region is a $V_h$ region comprising a first CDR comprising amino acids 31-35 of SEQ ID NO: 4, a second CDR comprising amino acids 50-66 of SEQ ID NO: 4, and a third CDR comprising amino acids 99-108 of SEQ ID NO: 4; and said second variable region is a $V_1$ region comprising a first CDR comprising amino acids 158-170 of SEQ ID NO: 4, a second CDR comprising amino acids 186-192 of SEQ ID NO: 4, and a third CDR comprising amino acids 225-235 of SEQ ID NO: 4.

2. The antibody or antigen binding fragment thereof of claim 1, wherein either:
   a) said first variable region consists of amino acids 1-119 of SEQ ID NO: 1 and said second variable region consists of amino acids 136-245 of SEQ ID NO: 1;
   b) said first variable region consists of amino acids 1-125 of SEQ ID NO: 2 and said second variable region consists of amino acids 142-251 of SEQ ID NO: 2;
   c) said first variable region consists of amino acids 1-119 of SEQ ID NO: 3 and said second variable region consists of amino acids 136-245 of SEQ ID NO: 3; or
   d) said first variable region consists of amino acids 1-119 of SEQ ID NO: 4 and said second variable region consists of amino acids 136-245 of SEQ ID NO: 4.

3. The antibody or antigen binding fragment thereof of claim 1, wherein said antibody is a monoclonal antibody.

4. The antibody or antigen binding fragment thereof of claim 1, wherein said binding protein is a single chain antibody wherein said first variable region is joined to said second variable region by an amino acid linker about 5 to 16 amino acids in length.

5. The antibody or antigen binding fragment thereof of claim 4, wherein either:
   a) said first variable region consists of amino acids 1-119 of SEQ ID NO: 1 and said second variable region consists of amino acids 136-245 of SEQ ID NO: 1;
   b) said first variable region consists of amino acids 1-125 of SEQ ID NO: 2 and said second variable region consists of amino acids 142-251 of SEQ ID NO: 2;
   c) said first variable region consists of amino acids 1-119 of SEQ ID NO: 3 and said second variable region consists of amino acids 136-245 of SEQ ID NO: 3; or
   d) said first variable region consists of amino acids 1-119 of SEQ ID NO: 4 and said second variable region consists of amino acids 136-245 of SEQ ID NO: 4.

6. An isolated single chain antibody that is any of SEQ ID NOs:1-4.

* * * * *

SEQUENCE LISTING

<160> NUMBER OF SEQ ID NOS: 9

<210> SEQ ID NO 1
<211> LENGTH: 245
<212> TYPE: PRT
<213> ORGANISM: Artificial Sequence
<220> FEATURE:
<223> OTHER INFORMATION: single-chain antibody

<400> SEQUENCE: 1

Glu Val Gln Leu Val Gln Ser Gly Ala Glu Val Arg Lys Pro Gly Ala
 1               5                  10                  15

Thr Val Lys Ile Ser Cys Lys Leu Thr Gly Asp Thr Phe Thr Asp Tyr
             20                  25                  30

Phe Ile Phe Trp Leu Gln Leu Ala Pro Gly Lys Gly Leu Gln Trp Met
         35                  40                  45

Gly Leu Ile Asp Pro Lys Asp Ala Gln Thr Ile Tyr Ala Glu Lys Phe
     50                  55                  60

Gln Gly Arg Val Ala Ile Thr Ala Asp Thr Ser Thr Asp Thr Ala Tyr
65                  70                  75                  80

Met Glu Val Ser Ser Leu Arg Ser Glu Asp Thr Ala Val Tyr Tyr Cys
                 85                  90                  95

Ala Thr Asp Ser Val Gly Ala Ala Gly Phe Asp Val Trp Gly Arg Gly
            100                 105                 110

Thr Met Val Thr Val Ser Ser Gly Gly Gly Ser Gly Gly Gly Gly
        115                 120                 125

Ser Gly Gly Gly Gly Ser Ala Leu Pro Val Leu Thr Gln Pro Pro Ser
    130                 135                 140

Ala Ser Gly Ala Pro Gly Gln Arg Val Thr Phe Ser Cys Ser Gly Ser
145                 150                 155                 160

Gly Ser Asn Ile Gly Ser Tyr Thr Val Asn Trp Tyr Gln Gln Leu Pro
                165                 170                 175

Gly Ala Ala Pro Arg Leu Leu Met His Thr Thr Asp Gln Arg Ala Ser
            180                 185                 190

Gly Ala Pro Asp Arg Phe Ser Gly Ser Lys Ser Gly Thr Ser Ala Ser
        195                 200                 205

Leu Ala Ile Thr Gly Leu Gln Ser Glu Asp Glu Ala Asp Tyr Phe Cys
    210                 215                 220

Ala Ala Trp Asp Asp Ser Leu Asp Gly Pro Val Phe Gly Gly Gly Thr
225                 230                 235                 240

Lys Leu Thr Val Leu
                245

<210> SEQ ID NO 2
<211> LENGTH: 251
<212> TYPE: PRT
<213> ORGANISM: Artificial Sequence
<220> FEATURE:
<223> OTHER INFORMATION: single-chain antibody

<400> SEQUENCE: 2

Gln Val Gln Leu Gln Glu Ser Gly Pro Gly Leu Val Lys Pro Ser Glu
 1               5                  10                  15

Thr Leu Ser Leu Asn Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
         35                  40                  45

```
Trp Ile Gly Ser Val Tyr Tyr Thr Gly Asn Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg His Val Leu Gly Gly Trp Glu Val Ser Gln Arg Phe
                100                 105                 110

Asp Tyr Trp Gly Arg Gly Thr Leu Val Thr Val Ser Ser Gly Gly Gly
            115                 120                 125

Gly Ser Gly Gly Gly Gly Ser Gly Gly Gly Gly Ser Ala Gln Ser Val
    130                 135                 140

Leu Thr Gln Pro Pro Ser Ala Ser Gly Thr Pro Gly Gln Arg Val Thr
145                 150                 155                 160

Ile Ser Cys Ser Gly Ser Ser Asn Ile Gly Ser Asn Pro Val Asn
                165                 170                 175

Trp Tyr Gln Gln Leu Pro Gly Thr Ala Pro Lys Leu Leu Ile His Thr
                180                 185                 190

Asn Asn Gln Arg Pro Ser Gly Val Pro Asp Arg Phe Ser Gly Ser Lys
                195                 200                 205

Ser Gly Thr Ser Ala Ser Leu Ala Ile Ser Gly Leu Leu Ser Glu Asp
    210                 215                 220

Glu Ala Asp Tyr Tyr Cys Ala Ala Trp Asp Asp Ser Leu Asn Ala Tyr
225                 230                 235                 240

Val Phe Gly Thr Gly Thr Lys Val Thr Val Leu
                245                 250

<210> SEQ ID NO 3
<211> LENGTH: 245
<212> TYPE: PRT
<213> ORGANISM: Artificial Sequence
<220> FEATURE:
<223> OTHER INFORMATION: single-chain antibody

<400> SEQUENCE: 3

Glu Val Gln Leu Val Glu Thr Gly Ala Glu Val Lys Lys Pro Gly Ser
1               5                   10                  15

Ser Val Lys Val Ser Cys Lys Ala Ser Gly Asp Thr Leu Ser Ser His
                20                  25                  30

Ala Ile Ile Trp Val Arg Gln Ala Pro Gly Gln Gly Leu Glu Trp Met
            35                  40                  45

Gly Gly Ile Ile Pro Ile Phe Arg Thr Val Asn Tyr Ala Gln Lys Phe
    50                  55                  60

Gln Gly Arg Val Thr Ile Thr Ala Asp Asp Ser Thr Ser Thr Ala Tyr
65                  70                  75                  80

Met Glu Leu Asn Asp Leu Arg Ser Glu Asp Thr Ala Val Tyr Tyr Cys
                85                  90                  95

Ala Lys Thr Leu Asn Glu Gly Leu Pro Trp Asp Tyr Trp Gly Gln Gly
                100                 105                 110

Thr Leu Val Thr Val Ser Ser Gly Gly Gly Ser Gly Gly Gly Gly
            115                 120                 125

Ser Gly Gly Gly Gly Ser Ala Gln Ser Val Leu Thr Gln Pro Pro Gly
    130                 135                 140

Ala Ser Gly Ala Pro Gly Gln Arg Val Thr Ile Ser Cys Ser Gly Asp
145                 150                 155                 160
```

```
Ser Ser Asn Ile Glu Ser Tyr Ala Val Asn Trp Tyr Gln Gln Val Pro
            165                 170                 175

Gly Met Ala Pro Lys Leu Leu Ile Tyr Arg Asp Asn Gln Arg Pro Ser
            180                 185                 190

Gly Val Pro Asp Arg Phe Ser Gly Ser Arg Ser Gly Thr Ser Ala Ser
            195                 200                 205

Leu Ala Ile Ser Gly Leu Gln Ser Glu Asp Glu Ala Asp Tyr Tyr Cys
            210                 215                 220

Gly Ser Trp Asp Asp Asn Leu Asn Gly Pro Thr Phe Gly Gly Gly Thr
225                 230                 235                 240

Lys Val Thr Val Leu
            245

<210> SEQ ID NO 4
<211> LENGTH: 245
<212> TYPE: PRT
<213> ORGANISM: Artificial Sequence
<220> FEATURE:
<223> OTHER INFORMATION: single-chain antibody

<400> SEQUENCE: 4

Glu Val Gln Leu Val Gln Ser Gly Ala Glu Val Arg Lys Pro Gly Thr
1               5                   10                  15

Ala Val Lys Ile Ser Cys Lys Val Ala Gly Asp Thr Phe Thr Asp Tyr
            20                  25                  30

Phe Ile Tyr Trp Leu Gln Gln Ala Pro Gly Lys Gly Pro Glu Trp Met
        35                  40                  45

Gly Leu Ile Asp Pro Lys Asp Ala Gln Thr Ile Tyr Ala Glu Lys Phe
50                  55                  60

Gln Gly Arg Val Ala Ile Thr Ala Asp Thr Ser Thr Asp Thr Ala Tyr
65                  70                  75                  80

Met Glu Leu Ser Ser Leu Lys Ser Glu Asp Thr Ala Val Tyr Tyr Cys
            85                  90                  95

Ala Thr Asp Ser Val Gly Ser Ala Gly Phe Asp Val Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Leu Pro Val Leu Thr Gln Pro Pro Ser
    130                 135                 140

Ala Ser Gly Ala Pro Gly Gln Arg Val Thr Phe Ser Cys Ser Gly Ser
145                 150                 155                 160

Gly Ser Asn Ile Gly Ser Tyr Thr Val Asn Trp Tyr Gln Gln Leu Pro
            165                 170                 175

Gly Ala Ala Pro Arg Leu Leu Met His Thr Thr Asp Gln Arg Ala Ser
            180                 185                 190

Gly Val Pro Asp Arg Phe Ser Gly Ser Lys Ser Gly Thr Ser Ala Ser
            195                 200                 205

Leu Ala Ile Thr Gly Leu Gln Ser Glu Asp Glu Ala Asp Tyr Phe Cys
            210                 215                 220

Ala Ala Trp Asp Asp Ser Leu Asp Gly Pro Val Phe Gly Gly Gly Thr
225                 230                 235                 240

Lys Leu Thr Val Leu
            245

<210> SEQ ID NO 5
<211> LENGTH: 735
<212> TYPE: DNA
```

<213> ORGANISM: Artificial Sequence
<220> FEATURE:
<223> OTHER INFORMATION: encoding SEQ ID NO: 1

<400> SEQUENCE: 5

```
gaagtgcagc tggtgcagtc tggggctgaa gtgaggaagc ctggggctac agtgaagatc      60
tcctgcaaat tgactggaga cacattcacc gactacttca tattttggct acaactggcc     120
cctggaaaag ggcttcagtg gatgggactt attgatccta agatgctca aacaatatat     180
gcagagaagt tccagggcag agtcgccatc accgcggaca cgtctaccga cacagcctac     240
atggaagtga gcagcctgag atctgaagac acggccgtct attactgtgc aacagattct     300
gtgggagctg ctggatttga tgtctggggc cgagggacaa tggtcaccgt ctcgagtgga     360
ggcggcggtt caggcggagg tggctctggc ggtggcggaa gtgcactgcc tgtgctgact     420
cagccccct cagcgtctgg ggcccccggg cagagggtca ccttctcttg ttctggaagc     480
ggctccaaca tcggaagtta tactgtaaac tggtaccagc agctcccagg agcggcccc     540
agactcctca tgcatactac tgatcagcgg gcctcagggg cgcctgaccg attctctggc     600
tccaagtctg gcacctcagc ctccctggcc atcactgggc tccagtctga ggatgaggct     660
gactatttct gtgcagcatg ggatgacagc ctggatggtc cggtgttcgg cggagggacc     720
aagctgaccg tccta                                                      735
```

<210> SEQ ID NO 6
<211> LENGTH: 753
<212> TYPE: DNA
<213> ORGANISM: Artificial Sequence
<220> FEATURE:
<223> OTHER INFORMATION: encoding SEQ ID NO: 2

<400> SEQUENCE: 6

```
caggtgcagc tgcaggagtc gggcccagga ctggtgaagc cttcggagac cctgtccctc      60
aactgcactg tctctggtgg ctccatcagc agtagtagtt actactgggg ctggatccgc     120
cagcccccag ggaaggggct ggagtggatt gggagtgtct attatactgg gaacacctac     180
tacaacccgt ccctcaagag tcgagtcacc atgtccgtcg acacgtccaa gaaccagttc     240
tccctgaagc tgaactccgt gaccgccgca gacacggctg tgtactattg tgcgagacat     300
gttttagggg gagggtggga agtaagtcag agatttgact actggggccg ggcaccctg     360
gtcaccgtct cgagtggagg cggcggttca ggcggaggtg gctctggcgg tggcggaagt     420
gcacagtctg tgttgacgca gccgccctca gcgtctggga ccccgggca gagggtcacc     480
atctcttgtt ctggaagcag ctccaacatc ggaagtaatc ctgtaaactg gtaccagcag     540
ctcccaggaa cggccccaa actcctcatc catactaaca atcagcggcc ctcagggtc     600
cctgaccgat tctctggctc caagtctggc acctcagcct ccctggccat cagtgggctc     660
ctgtctgagg atgaggctga ttattactgt gcagcatggg atgacagcct gaatgcttat     720
gtcttcggaa ctgggaccaa ggtcaccgtc cta                                  753
```

<210> SEQ ID NO 7
<211> LENGTH: 735
<212> TYPE: DNA
<213> ORGANISM: Artificial Sequence
<220> FEATURE:
<223> OTHER INFORMATION: encoding SEQ ID NO: 3

<400> SEQUENCE: 7

```
gaggtgcagc tggtggagac tggggctgag gtgaagaagc ctgggtcctc ggtgaaggtc      60
```

```
tcctgcaagg cttccggaga caccctcagc agtcatgcta tcatctgggt gcgacaggcc    120
cctggacaag ggcttgagtg gatgggaggg atcatcccta tctttcgtac agtaaattac    180
gcacagaaat tccagggcag agtcacgatt accgcggacg attccacgag cacggcctac    240
atggaactca atgacttgag atctgaggac acggccgtct attactgtgc gaaaacgcta    300 aatgagggt taccgtggga ctactggggc cagggcaccc tggtcaccgt ctcgagtgga    360
ggcggcggtt caggcggagg tggctctggc ggtggcggaa gtgcacagtc tgtgctgact    420
cagccacccg agcgtctggg gcccccggg cagagggtca ccatctcttg ttctggagac    480
agttccaaca tcgagagtta tgctgtaaat tggtaccagc aagtccctgg aatggccccc    540
aaactcctca tctatcgtga taatcagcgc ccctcagggg tccctgaccg attctctggc    600
tccaggtctg gcacctcagc ctccctggcc atcagtgggc tccagtctga ggatgaggct    660
gattattact gtggatcatg ggatgacaat ttgaatggcc ccacgttcgg cggagggacc    720
aaggtcaccg tccta    735
```

```
<210> SEQ ID NO 8
<211> LENGTH: 735
<212> TYPE: DNA
<213> ORGANISM: Artificial Sequence
<220> FEATURE:
<223> OTHER INFORMATION: encoding SEQ ID NO: 4

<400> SEQUENCE: 8
gaggtgcagc tggtgcagtc tggggctgag gtgaggaagc ctgggactgc agtgaaaatc     60
tcctgcaagg ttgctggcga cacattcacc gactacttca tatactggct gcaacaggcc    120
cctggaaaag ggcctgagtg gatgggactt attgatccta aggatgctca gacaatatac    180
gcagagaagt tccagggcag agtcgccata accgcggaca cgtctacgga cacagcttac    240 atgaactga gcagcctgaa gtctgaggac acggccgtgt attactgtgc aacagattct    300
gtgggatctg ctggttttga tgtctggggc cagggcaccc tggtcaccgt ctcgagtgga    360
ggcggcggtt caggcggagg tggctctggc ggtggcggaa gtgcactgcc tgtgctgact    420 cagccccccct cagcgtctgg ggcccccggg cagagggtca ccttctcttg ttctggaagc    480
ggctccaaca tcggaagtta tactgtaaac tggtaccagc agctcccagg agcggccccc    540
agactcctca tgcatactac tgatcagcgg gcctcagggg tgcctgaccg attctctggc    600
tccaagtctg gcacctcagc ctccctggcc atcactgggc tccagtctga ggatgaggct    660
gactatttct gtgcagcatg ggatgacagc ctgatggtc cggtgttcgg cggagggacc    720
aagctgaccg tccta    735
```

```
<210> SEQ ID NO 9
<211> LENGTH: 509
<212> TYPE: PRT
<213> ORGANISM: human

<400> SEQUENCE: 9

Met Gly Cys Ser Ala Lys Ala Arg Trp Ala Ala Gly Ala Leu Gly Val
 1               5                   10                  15

Ala Gly Leu Leu Cys Ala Val Leu Gly Ala Val Met Ile Val Met Val
            20                  25                  30

Pro Ser Leu Ile Lys Gln Gln Val Leu Lys Asn Val Arg Ile Asp Pro
        35                  40                  45

Ser Ser Leu Ser Phe Asn Met Trp Lys Glu Ile Pro Ile Pro Phe Tyr
    50                  55                  60
```

-continued

Leu Ser Val Tyr Phe Phe Asp Val Met Asn Pro Ser Glu Ile Leu Lys
65                  70                  75                  80

Gly Glu Lys Pro Gln Val Arg Glu Arg Gly Pro Tyr Val Tyr Arg Glu
                85                  90                  95

Phe Arg His Lys Ser Asn Ile Thr Phe Asn Asn Asp Thr Val Ser
            100                 105                 110

Phe Leu Glu Tyr Arg Thr Phe Gln Phe Gln Pro Ser Lys Ser His Gly
            115                 120                 125

Ser Glu Ser Asp Tyr Ile Val Met Pro Asn Ile Leu Val Leu Gly Ala
        130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
                180                 185                 190

Lys Tyr Phe Pro Gly Met Phe Pro Phe Lys Asp Lys Phe Gly Leu Phe
            195                 200                 205

Ala Glu Leu Asn Asn Ser Asp Ser Gly Leu Phe Thr Val Phe Thr Gly
        210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
            260                 265                 270

Glu Phe Tyr Ser Pro Glu Ala Cys Arg Ser Met Lys Leu Met Tyr Lys
            275                 280                 285

Glu Ser Gly Val Phe Glu Gly Ile Pro Thr Tyr Arg Phe Val Ala Pro
        290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
            340                 345                 350

Val Leu Ala Glu Ala Val Thr Gly Leu His Pro Asn Gln Glu Ala His
            355                 360                 365

Ser Leu Phe Leu Asp Ile His Pro Val Thr Gly Ile Pro Met Asn Cys
        370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
                405                 410                 415

Ala Glu Ser Gly Ala Met Glu Gly Glu Thr Leu His Thr Phe Tyr Thr
            420                 425                 430

Gln Leu Val Leu Met Pro Lys Val Met His Tyr Ala Gln Tyr Val Leu
            435                 440                 445

Leu Ala Leu Gly Cys Val Leu Leu Val Pro Val Ile Cys Gln Ile
        450                 455                 460

Arg Ser Gln Glu Lys Cys Tyr Leu Phe Trp Ser Ser Lys Lys Gly
465                 470                 475                 480

Ser Lys Asp Lys Glu Ala Ile Gln Ala Tyr Ser Glu Ser Leu Met Thr
            485                 490                 495

```
Ser Ala Pro Lys Gly Ser Val Leu Gln Glu Ala Lys Leu
            500                 505
```